(12) United States Patent
Pullen

(10) Patent No.: US 6,500,445 B1
(45) Date of Patent: Dec. 31, 2002

(54) CONTROLLING DUST MITES WITH A COMPOSITION CONTAINING SURFACTANTS, HIGH TERPENE OIL AND MONOHYDRIC ALCOHOL

(76) Inventor: Erroll M. Pullen, 277 Raleigh Quay, Grand Cayman, B.W.I. (ZA)

( * ) Notice: Subject to any disclaimer, the term of this patent is extended or adjusted under 35 U.S.C. 154(b) by 0 days.

(21) Appl. No.: 09/587,595

(22) Filed: Jun. 5, 2000

Related U.S. Application Data

(63) Continuation-in-part of application No. 09/418,058, filed on Oct. 14, 1999, now Pat. No. 6,277,389, which is a continuation-in-part of application No. 09/282,903, filed on Mar. 31, 1999, now Pat. No. 6,258,369.

(51) Int. Cl.⁷ .......................... A61K 7/08; A61K 7/075; A61L 9/01; A01N 25/00
(52) U.S. Cl. .................. 424/405; 424/70.19; 424/76.8; 514/975
(58) Field of Search ................. 435/405, 424, 435/243, 325, 262.5, 262; 424/70.19, 76.8, 405; 514/975

(56) References Cited

U.S. PATENT DOCUMENTS

| | | | | |
|---|---|---|---|---|
| 5,110,804 A | * | 5/1992 | Lee | 514/60 |
| 5,753,593 A | * | 5/1998 | Pullen et al. | 504/150 |
| 5,977,186 A | * | 11/1999 | Franklin | 514/690 |
| 6,093,856 A | * | 7/2000 | Cripe et al. | 568/625 |
| 6,130,253 A | * | 10/2000 | Franklin et al. | 514/690 |
| 6,248,710 B1 | * | 6/2001 | Bijsterbosch et al. | 510/470 |

* cited by examiner

*Primary Examiner*—David M. Naff
*Assistant Examiner*—Deborah K. Ware
(74) *Attorney, Agent, or Firm*—A. W. Fisher, III

(57) ABSTRACT

Methods and compositions are provided for treating clothing, pillows, bedding, furniture, rugs or carpets for dust mites. Non-toxic aqueous compositions contain one or more surfactants high terpene oils and a monohydric alcohol. Various percentage weight amounts such as 17 to 27 percent of surfactants, 8 to 16 percent of high terpene oils, 4 to 8 percent monohydric and water are comprised by a composition for treating and controlling dust mites on clothing, pillows, bedding, furniture, rugs or carpets. A method for controlling and treating dust mites includes applying an effective amount of a non-toxic aqueous composition, scrubbing the composition into the clothing, pillows, bedding, furniture, rugs or carpets and rinsing the composition and dust mites therefrom.

20 Claims, No Drawings

CONTROLLING DUST MITES WITH A COMPOSITION CONTAINING SURFACTANTS, HIGH TERPENE OIL AND MONOHYDRIC ALCOHOL

CROSS REFERENCE

This is a continuation-in-part application of application Ser. No. 09/418,058 filed Oct. 14, 1999 now U.S. Pat. No. 6,277,389, which is a continuation in part of application Ser. No. 09/282,963 filed Mar. 31, 1999, now U.S. Pat. No. 6,258,369.

BACKGROUND OF THE INVENTION

A non-toxic aqueous pesticide to effectively control dust mites.

FIELD OF THE INVENTION

Various parasites such as lice, ticks, mites, aphides and chiggers attack untreated and unprotected animals and plants. Poultry are particularly susceptible to parasitic infestations, both internal and external, If left uncontrolled, poultry diseases and parasites can result in reduced productivity and high mortality rates. Thus, effective management and sanitation practices, vaccination and medication are essential to prevent and control diseases and pests.

Where poultry is involved, the larvae of these pests attach to the wings and parts of the body injecting a poisonous substance that irritates the skin and causes itching. Such infestation is manifest in lesions observable when birds are dressed. This, of course, reduces the value of the poultry. Moreover, the young birds become droopy, refuse to eat and can die.

In the past, various oils have been used to control insects and mites. Recently, however, renewed attention has focused on the use of oils as a natural substitute for traditional insecticides with attendant toxic and other dangerous side effects.

These oils include horticultural oils which are highly refined petroleum products than can be mixed with water for application for control of target insect and mite pests without deleterious effects. Modern horticultural oils do not include vegetable, fish or whale oils.

Horticultural spray oils are the low toxicity alternative to broad spectrum insecticides. Since the mechanism of insect and mite control with spray oils is by suffocation and/or repellency of egg laying females, there is no requirement for the addition of toxic chemicals. These properties are a valuable and well recognized component of the practice of integrated pest management where oil spraying is intrinsically linked to natural control of pests by predators and parasitoids. Horticultural spray oils are formulated on highly refined clear oil with a minimum of nonionic surfactant. Independent environmental impact studies have shown that D-C-TRON has no detrimental effect on the environment. Mammalian toxicity studies published in the American Journal of Industrial Medicine have shown that oils at this refinement level are non-toxic and non-carcinogenic.

Aqueous suspensions of malathion, stirofos, Ravap and carbaryl formulations (0.25 to 1.0 per cent) have been tested as dips for control of the northern foul mite (NFM), Ornithonyssus sylviarum (Canestrini and Fanzago) on caged White Leghorn hens. Hens treated with Ravap showed symptoms of organophosphorus insecticide poisoning soon after treatment and some died as a result of the dip. However, dipping with the other insecticides did not result in any apparent toxic effects. Malathion was observed to provide residual control of mites for about 4 weeks post-treatment, but both stirofos and carbaryl dips gave complete control for at least 6 weeks against repeated challenges with the NFM. There were no significant differences in the percent hen-day egg production, feed consumption, or body weight of the hens that could be attributed to any of the chemical treatments.

Generally, oil sprays are safe to humans. These oil sprays have little, if any, negative effect on wildlife and non-target insects in the environment. Furthermore, oil sprays are less toxic due to the method by which they kill target pests. In particular, the thin film of oil covers the target insect or mite and plugs the spiracles or pores through which the pests or parasites breathe. The cause of death is primarily suffocation. Large, motile insects and animals that breathe by another method are not affected by these oils.

Another advantage of oil applications is the absence of objectionable odors. In addition, oils are relatively inexpensive and significantly less expensive than many insecticides.

Unfortunately, there are limitations to the use of oil treatments. For example, oils are only effective against those pests that are thoroughly coated by the spray insolution. This usually means that only small, immobile or slow moving pests that are exposed on the surface of the poultry, animal or plant at the time of application will be controlled.

Since oil sprays only work by contracting and covering the target pest, thorough application is essential. Missed surface areas provide a safe refuge for the target pests.

U.S. Pat. No. 5,693,344 shows a hazard-free method for controlling insects using a non-toxic composition in the form of a fragrance and crystalline particles which puncture directly through the exoskeleton of an insect. In operation, the particles work themselves between the insects protective body plates and then puncture the exoskeleton permitting entry of the fragrance into the body of the insect. Once inside, the particles absorb up to four times their weight of the vital body fluids of the insect and the fragrance has a neural effect on the insect.

Thus, there remains a need for a non-toxic pesticide that can be effectively applied to control or kill dust mites without the danger of a toxic reaction by humans or pet animals.

SUMMARY OF THE INVENTION

The present invention relates to a non-toxic aqueous pesticide and method of application to effectively control dust mites found in clothing, pillows, bedding, furniture and rugs or carpets comprising at least one surfactant and at least one terpene containing oil.

High terpene containing natural oil as used herein means those natural oils having a terpene content of at least 50 per cent. It is preferable that the high terpene natural oil contains at least 80 per cent. Suitable high terpene containing natural oils includes oil from conifers such as citrus peel oils, preferably orange oil, grapefruit oil, lemon oil or pine oil. Of these, cold pressed orange oil is the most preferred. Naturally, the amount of high terpene containing natural oils in the non-toxic aqueous pesticide will depend upon the amount of terpenes in the specific oil used.

The surfactant may comprise conventional surfactants such as anionic and nonionic surfactants.

The non-toxic aqueous pesticide may also contain various additives such as antioxidants, preservatives, pH neutralizers and/or clarifiers.

Since the non-toxic aqueous pesticide is an aqueous composition, the balance of the non-toxic aqueous pesticide is water.

In use, the non-toxic aqueous pesticide is diluted from about 2 per cent to about 7 per cent solution but preferably about 5 per cent solution and applied to the surface of the pillows, bedding, furniture and rugs or carpets or used to launder or wash clothing, pillow slips or similar fabric products. After the pesticide has been so applied or used, the pesticide residue is rinsed or removed. In some cases, repeated applications may be required.

When so applied, the non-toxic aqueous pesticide is effective in controlling dust mites. The mechanism of insect and mite control is believed to be by suffocation and/or the dissolving of the waxy layers of the insect's exoskeleton. There is no requirement for the addition of toxic chemicals thereby causing an imbalance in the insect and/or parasites delicate body moisture balance. As such, the instant invention provides a virtually non-toxic alternative to broad spectrum insecticides.

The invention accordingly comprises the features of construction, combination of elements, and arrangement of parts which will be exemplified in the construction hereinafter set forth, and the scope of the invention will be indicated in the claims.

DETAILED DESCRIPTION OF THE PREFERRED EMBODIMENT

The present invention relates to an environmentally compatible non-toxic aqueous pesticide comprising at least one surfactant and at least one high terpene containing oil to effectively control dust mites found on clothing, pillows, bedding, furniture and rugs or carpets. The invention also includes a method of application of the non-toxic aqueous pesticide.

High terpene containing natural oil as used herein means those natural oils having a terpene content of at least 50 per cent. It is preferable that the high terpene natural oil contains at least 80 per cent. Suitable high terpene containing natural oils includes oil from conifers such as citrus peel oils, preferably orange oil, grapefruit oil, lemon oil, or pine oil. Of these, orange oil is preferred and cold pressed orange oil the most preferred. The preferred terpene content is from about 80 per cent to about 90 per cent and most preferred from about 85 per cent to about 87 per cent by weight.

Naturally, the amount of high terpene containing natural oils in the non-toxic aqueous pesticide will depend upon the amount of terpenes in the specific oil used. Generally, the non-toxic pesticide composition contains from about 8 per cent to about 16 per cent by weight of high terpene containing natural oil, preferably about 12 per cent by weight.

While not to be bound by theory, it is believed that the terpenes in the natural oils provide a mechanism for the efficacy of the instant invention. In particular, the thin film of oil covers the mites and plugs the spiracles or pores through which such mites breathe. Thus the cause of death may be suffocation. The non-toxic aqueous pesticide may also breakdown or dissolve the exoskeleton of the mites. Further, since the high terpene containing oils are natural oils, the non-toxic aqueous pesticide is environmentally acceptable and has little, if any deleterious effect on wildlife and non-target insects.

Surfactants such as anionic and nonionic surfactants are acceptable for use in the non-toxic aqueous pesticide of the present invention. Preferred are anionic surfactants such as salts of fatty acids, alkyl sulphates, alkyl ether sulphonates and alkyl aryl sulphonates. Examples of preferred surfactants include from about 3 per cent to about 6 per cent dodecylbenzene sulfonic acid, from about 4.5 per cent to about 8.5 per cent sodium laurel sulfate, from about 5 per cent to about 10 per cent alcohol ethoxylate and from about 0.9 per cent to about 2.0 per cent olefin sulfonate.

Generally, the non-toxic aqueous pesticide will contain from about 17 per cent to about 27 per cent by weight of surfactant(s) and preferably from about 20 per cent to about 25 per cent by weight.

The non-toxic aqueous pesticide also contains from about 4 per cent to about 8 per cent by weight and preferably 6 per cent by weight of a monohydric alcohol such as ethanol.

The non-toxic aqueous pesticide may also contain various additives such as preservatives, pH neutralizers and/or clarifiers or stabilizers.

Such preservatives may include butylated hydroxytoluene (BHT), p-hydroxybenzoic acid, fungicide and bactericide. The butylated hydroxytoluene (BHT) acts as an antioxidant. The antioxidant range from about 0.01 per cent to about 1.0 per cent by weight and preferably about 0.09 per cent by weight. The fungicide such as Borax 10 mole or sodium tetraborate decahydrate is from about 0.50 per cent to about 1.0 per cent by weight and preferably about 0.72 per cent by weight. The preservative such as p-hydroxybenzoic acid is from about 0.35 per cent to about 0.85 per cent by weight and preferably about 0.54 per cent by weight. The bactericide such as Dowicil 75 is from about 0.06 per cent to about 0.10 per cent by weight and preferably about 0.08 per cent by weight.

Caustic crystals such as sodium hydroxide may be added in an amount from about 1.0 per cent to about 1.5 per cent by weight to neutralize the composition and preferably about 1.23 per cent by weight.

An example of a suitable clarifier or stabilizer is urea in an amount from about 0.4 per cent to about 1.2 per cent by weight and preferably about 0.81 per cent by weight.

The balance of the non-toxic aqueous pesticide is water.

The preferred non-toxic aqueous pesticide comprises about 12 per cent cold pressed orange oil with from about 85 per cent to about 87 per cent terpene content by weight, about 6.5 per cent sodium lauryl sulfate, about 7.6 per cent of alcohol ethoxylate, about 1.6 per cent olefin sulfonate, about 4.5 per cent dodecylbenzene sulphonic acid and about 6 per cent ethanol with the balance a diluent such as water, all by weight.

The non-toxic aqueous pesticide may further include about 0.09 per cent butylated hydroxytoluene, about 0.54 per cent p-Hydroxybenzoic acid, about 0.08 per cent bactericide, about 0.72 per cent fungicide, about 0.81 per cent urea and/or about 1.23 per cent sodium hydroxide.

In use, the non-toxic aqueous pesticide is diluted with water and applied to the surface of the bedding, carpets, upholstery, pillows or the like, or used to launder or wash clothing, pillow slips and other fabric products. After the pesticide has been so applied or used, the pesticide residue is rinsed or removed. An effective dilution rate is from about 2 per cent to about 7 per cent but preferably 5 per cent by weight, i.e. 5 per cent composition is diluted with a balance of water by weight. In some cases, repeated applications may be required.

When so applied, the non-toxic aqueous pesticide has been effective in controlling dust mites. Since the mechanism of mite control appears to be by suffocation and/or breakdown the waxy layer on the exoskeleton, there is no requirement for the addition of toxic chemicals. As such, the instant invention provides a virtually non-toxic alternative as applied to broad-spectrum insecticides.

About 0.001 per cent by weight of a colorant such as FD and C may be added.

While the invention has been described above with respect to certain particular embodiments thereof, numerous other forms and modifications will be apparent to those skilled in the art. The appended claims and the invention generally should be construed as covering all such obvious forms and modifications which are within the true spirit and scope of the invention.

What is claimed is:

1. A non-toxic aqueous composition for treating clothing, pillows, bedding, furniture, rugs or carpets to effectively control dust mites, said composition comprising at least one surfactant selected from the group consisting of sodium laurel sulphate, alcohol ethoxylate, olefin sulphonate, sulphonic acid and mixtures thereof, at least one high terpene containing natural oil selected from the group consisting of citrus peel oils, pine oils and mixtures thereof and a monohydric alcohol, said non-toxic aqueous composition containing from about 17 percent to about 27 percent of said at least one surfactant by weight percent, from about 8 percent to about 16 percent of said at least one high terpene containing natural oil by weight percent and from about 4 percent to about 8 percent of monohydric alcohol by weight percent with the balance water.

2. The composition of claim 1 wherein said non-toxic aqueous composition contains from about 20 percent to about 25 percent said at least one surfactant by weight percent, about 12 percent of said at least one high terpene containing natural oil by weight percent and about 6 percent of monohydric alcohol by weight percent.

3. The composition of claim 2 wherein said non-toxic aqueous composition further contains butylated hydroxytoluene from about 0.01 percent to about 1.0 percent by weight percent, sodium tetraborate decahydrate from about 0.50 percent to about 1.0 percent by weight percent, p-hydroxybenzoic acid from about 0.35 percent to about 0.85 percent by weight percent and bactericide from about 0.06 percent to about 0.10 percent by weight percent.

4. The composition of claim 1 wherein said non-toxic aqueous composition is diluted with water at a dilution rate of at least about 2 percent of said non-toxic aqueous composition by weight percent.

5. The composition of claim 1 wherein said composition is diluted with water at a dilution rate of about 5 percent by weight of said non-toxic aqueous composition by weight percent.

6. A non-toxic aqueous composition for treating clothing, pillows, bedding, furniture, rugs or carpets to effectively control dust mites by, said composition comprising at least one surfactant selected from the group consisting of sodium laurel sulphate, alcohol ethoxylate, olefin sulphonate, sulphonic acid and mixtures thereof, at least one high terpene containing natural oil selected from the group consisting of citrus peel oils, pine oils and mixtures thereof and a monohydric alcohol, said non-toxic aqueous composition containing from about 3 percent to about 6 percent dodecylbenzene sulfonic acid by weight percent, from about 4.5 percent to about 8.5 percent sodium laurel sulfate by weight percent, from about 5 percent to about 10 percent alcohol ethoxylate by weight percent and from about 0.9 percent to about 2.0 percent olefin sulfonate by weight percent; 12 percent by weight percent said at least one high terpene containing natural oil and about 4 to 8 percent ethanol by weight percent with the balance water.

7. A non-toxic aqueous composition for treating clothing, pillows, bedding, furniture, rugs or carpets to effectively control dust mites, said composition comprising at least one surfactant selected from the group consisting of sodium laurel sulphate, alcohol ethoxylate, olefin sulphonate, sulphonic acid and mixtures thereof, at least one high terpene containing natural oil selected from the group consisting of citrus peel oils, pine oils and mixtures thereof and a monohydric alcohol, said non-toxic aqueous composition comprises about 12 percent cold pressed orange oil, about 6.5 percent sodium lauryl sulfate by weight percent, about 7.6 percent of alcohol ethoxylate by weight percent, about 1.6 percent olefin sulfonate by weight percent, about 4.5 percent dodecylbenzene sulphonic acid by weight percent, about 6 percent ethanol by weight percent and the balance water.

8. The composition of claim 7 wherein said non-toxic aqueous composition further contains about 0.09 percent butylated hydroxytoluene by weight percent, about 0.54 percent p-Hydroxybenzoic acid by weight percent, about 0.08 percent bactericide by weight percent, about 0.72 percent fungicide by weight percent, about 0.81 percent urea by weight percent, and about 1.23 percent sodium hydroxide by weight percent.

9. The composition of claim 7 wherein said non-toxic aqueous composition is diluted with water at a dilution rate of from about 2 percent to about 7 percent of said non-toxic aqueous composition by weight percent.

10. The composition of claim 7 wherein said non-toxic aqueous composition is diluted with water at a dilution rate of about at least 5 percent of said non-toxic aqueous composition by weight percent.

11. A method for treating clothing, pillows, bedding, furniture, rugs or carpets to effectively control dust mites by (a) applying an effective amount of a non-toxic aqueous composition comprising at least one surfactant selected from the group consisting of sodium laurel sulphate, alcohol ethoxylate, olefin sulphonate, sulphonic acid and mixtures thereof, at least one high terpene containing natural oil selected from the group consisting of citrus peel oils, pine oils and mixtures thereof and a monohydric alcohol to the surface of clothing, pillows, bedding, furniture, rugs or carpets, (b) scrubbing said non-toxic aqueous composition into the clothing, pillows, bedding, furniture, rugs or carpets and (c) rinsing said non-toxic aqueous composition and dust mites from the clothing, pillows, bedding, furniture, rugs or carpets, said non-toxic aqueous composition containing from about 17 percent to about 27 percent of said at least one surfactant by weight percent, from about 8 percent to about 16 percent of said at least one high terpene containing natural oil by weight percent, from about 4 percent to about 8 percent of monohydric alcohol by weight percent and the balance water.

12. The method of claim 11 wherein said non-toxic aqueous composition contains from about 20 percent to about 25 percent of said at least one surfactant by weight percent, about 12 percent of said at least one high terpene containing natural oil by weight percent and about 6 percent of monohydric alcohol by weight percent.

13. The method of claim 12 wherein said non-toxic aqueous composition further contains butylated hydroxytoluene from about 0.01 percent to about 1.0 percent by weight percent, sodium tetraborate decahydrate from about 0.50 percent to about 1.0 percent by weight percent, p-hydroxybenzoic acid from about 0.35 percent to about 0.85 percent by weight percent and bactericide from about 0.06 percent to about 0.10 percent by weight percent.

14. The method of claim 11 wherein said non-toxic aqueous composition is diluted with water at a the dilution rate of at least about 2 percent of said non-toxic aqueous composition by weight percent.

15. The method of claim 11 wherein said composition is diluted with water at a dilution rate of about 5 percent by weight of said non-toxic aqueous composition by weight percent.

16. A method for treating clothing, pillows, bedding, furniture, rugs or carpets to effectively control dust mites by (a) applying an effective amount of non-toxic aqueous composition comprising at least one surfactant selected from the group consisting of sodium laurel sulphate, alcohol ethoxylate, olefin sulphonate, sulphonic acid and mixtures thereof, at least one high terpene containing natural oil selected from the group consisting of citrus peel oils, pine oils and mixtures thereof and a monohydric alcohol to the surface of clothing, pillows, bedding, furniture, rugs or carpets, (b) scrubbing said non-toxic aqueous composition into the clothing, pillows, bedding, furniture, rugs or carpets and (c) rinsing said non-toxic aqueous composition and dust mites from the clothing, pillows, bedding, furniture, rugs or carpets said non-toxic aqueous composition containing from about 3 percent to about 6 percent dodecylbenzene sulfonic acid by weight percent, from about 4.5 percent to about 8.5 percent sodium laurel sulfate by weight percent, from about 5 percent to about 10 percent alcohol ethoxylate by weight percent and from about 0.9 percent to about 2.0 percent olefin sulfonate by weight percent; 12 percent by weight percent of said at least one high terpene containing natural oil and about 4 to 8 percent ethanol by weight percent with the balance water.

17. A method for treating clothing, pillows, bedding, furniture, rugs or carpets to effectively control dust mites by (a) applying an effective amount of non-toxic aqueous composition comprising at least one surfactant selected from the group consisting of sodium laurel sulphate, alcohol ethoxylate, olefin sulphonate, sulphonic acid and mixtures thereof, at least one high terpene containing natural oil selected from the group consisting of citrus peel oils, pine oils and mixtures thereof and a monohydric alcohol to the surface of clothing, pillows, bedding, furniture, rugs or carpets, (b) scrubbing said non-toxic aqueous composition into the clothing, pillows, bedding, furniture, rugs or carpets and (c) rinsing said non-toxic aqueous composition and dust mites from the clothing, pillows, bedding, furniture, rugs or carpets, said non-toxic aqueous composition comprises about 12 percent orange oil by weight percent, about 6.5 percent sodium lauryl sulfate by weight percent, about 7.6 percent of alcohol ethoxylate by weight percent, about 1.6 percent olefin sulfonate by weight percent, about 4.5 percent dodecylbenzene sulphonic acid by weight percent, about 6 percent ethanol by weight percent and the balance water.

18. The method of claim 17 wherein said non-toxic aqueous composition further contains about 0.09 percent butylated hydroxytoluene by weight percent, about 0.54 percent p-Hydroxybenzoic acid by weight percent, about 0.08 percent bactericide by weight percent, about 0.72 percent fungicide by weight percent, about 0.81 percent urea by weight percent, and about 1.23 percent sodium hydroxide by weight percent.

19. The method of claim 17, wherein said non-toxic aqueous composition is diluted with water at a dilution rate of from about 2 percent to about 7 percent of said non-toxic aqueous composition by weight percent.

20. The method of claim 17, wherein said non-toxic aqueous composition is diluted with water at a dilution rate of about at least 5 percent of said non-toxic aqueous composition by weight percent.

\* \* \* \* \*